US008263169B2

(12) United States Patent
Tang et al.

(10) Patent No.: US 8,263,169 B2
(45) Date of Patent: Sep. 11, 2012

(54) STENT MANDREL FIXTURE AND METHOD FOR REDUCING COATING DEFECTS

(75) Inventors: Fuh-Wei Tang, Temecula, CA (US);
Syed F. A. Hossainy, Fremont, CA (US);
Dorie Happ, Redwood City, CA (US);
Ty T. Hu, Pembroke Pines, FL (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 14 days.

(21) Appl. No.: 12/246,423

(22) Filed: Oct. 6, 2008

(65) Prior Publication Data
US 2009/0053393 A1 Feb. 26, 2009

Related U.S. Application Data

(62) Division of application No. 10/255,913, filed on Sep. 26, 2002, now Pat. No. 7,776,381.

(51) Int. Cl.
*B05B 13/02* (2006.01)
*B05C 13/00* (2006.01)
*B05D 3/00* (2006.01)

(52) U.S. Cl. ....... 427/2.1; 427/2.24; 427/2.25; 118/319; 118/320; 118/500; 118/501

(58) Field of Classification Search .......... 118/500, 118/501; 427/2.1–2.28
See application file for complete search history.

(56) References Cited

U.S. PATENT DOCUMENTS

| | | | |
|---|---|---|---|
| 4,733,665 A | 3/1988 | Palmaz | |
| 4,800,882 A | 1/1989 | Gianturco | |
| 4,886,062 A | 12/1989 | Wiktor | |
| 4,906,423 A | 3/1990 | Frisch | |
| 5,037,427 A | 8/1991 | Harada et al. | |
| 5,234,457 A | 8/1993 | Andersen | |
| 5,537,729 A | 7/1996 | Kolobow | |
| 5,628,786 A | 5/1997 | Banas et al. | |
| 5,735,897 A | 4/1998 | Buirge | |
| 5,772,864 A | 6/1998 | Møller et al. | |
| 5,788,626 A | 8/1998 | Thompson | |
| 5,895,407 A | 4/1999 | Jayaraman | |
| 5,897,911 A | 4/1999 | Loeffler | |
| 5,911,752 A | 6/1999 | Dustrude et al. | |
| 5,922,393 A | 7/1999 | Jayaraman | |
| 5,935,135 A | 8/1999 | Bramfitt et al. | |
| 6,010,573 A | 1/2000 | Bowlin | |
| 6,056,993 A | 5/2000 | Leidner et al. | |
| 6,120,847 A | 9/2000 | Yang et al. | |
| 6,126,686 A | 10/2000 | Badylak et al. | |
| 6,153,252 A | 11/2000 | Hossainy et al. | |
| 6,156,373 A | 12/2000 | Zhong et al. | |
| 6,214,115 B1 | 4/2001 | Taylor et al. | |
| 6,245,099 B1 * | 6/2001 | Edwin et al. | 623/1.13 |
| 6,258,121 B1 | 7/2001 | Yang et al. | |
| 6,322,847 B1 | 11/2001 | Zhong et al. | |
| 6,364,903 B2 | 4/2002 | Tseng et al. | |
| 6,387,118 B1 | 5/2002 | Hanson | |
| 6,521,284 B1 | 2/2003 | Parsons et al. | |
| 6,527,863 B1 * | 3/2003 | Pacetti et al. | 118/500 |
| 6,565,659 B1 | 5/2003 | Pacetti et al. | |
| 6,572,644 B1 * | 6/2003 | Moein | 623/1.11 |

(Continued)

*Primary Examiner* — Timothy Meeks
*Assistant Examiner* — Cachet Sellman
(74) *Attorney, Agent, or Firm* — Squire Sanders (US) LLP

(57) ABSTRACT

A stent mandrel fixture for supporting a stent during the application of a coating substance is provided.

48 Claims, 3 Drawing Sheets

U.S. PATENT DOCUMENTS

| | | |
|---|---|---|
| 6,599,288 B2 * | 7/2003 | Maguire et al. ................. 606/27 |
| 6,605,154 B1 | 8/2003 | Villareal |
| 6,673,154 B1 | 1/2004 | Pacetti et al. |
| 6,682,771 B2 | 1/2004 | Zhong et al. |
| 6,695,920 B1 | 2/2004 | Pacetti et al. |
| 6,818,063 B1 * | 11/2004 | Kerrigan ....................... 118/500 |
| 7,402,329 B2 | 7/2008 | Pacetti et al. |
| 2002/0147490 A1 | 10/2002 | Pletzer et al. |
| 2003/0113439 A1 | 6/2003 | Pacetti et al. |

* cited by examiner

STENT MANDREL FIXTURE AND METHOD FOR REDUCING COATING DEFECTS

This application is a divisional application of U.S. application Ser. No. 10/255,913, filed Sep. 26, 2002, which is incorporated herein by reference in its entirety.

TECHNICAL FIELD

This invention relates generally to stent mandrel fixtures, and more particularly, but not exclusively, provides a stent mandrel fixture and method for reducing coating defects on stents.

BACKGROUND

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is the potential for coating defects. While some coating defects can be minimized by adjusting the coating parameters, other defects occur due to the nature of the interface between the stent and the apparatus on which the stent is supported during the coating process. A high degree of surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the coating from the stent and leaving bare areas. Alternatively, the excess coating may stick to the stent, thereby leaving excess coating as clumps or pools on the struts or webbing between the struts.

Accordingly, a new stent mandrel fixture is needed to minimize coating defects.

SUMMARY

In accordance with one embodiment, a stent mandrel fixture for supporting a stent during application of a coating substance to the stent is provided, comprising: a first member for supporting a first end of the stent, at least a portion of the first member being made from or being coated with a non-stick material for preventing the coating substance from adhering to the first member; a second member for supporting a second end of the stent, at least a portion of the second member being made from or being coated with the non-stick material; and a third member connecting the first member to the second member and extending through a longitudinal bore of the stent. The first or second member can have a domed shaped end, a flat end or can have grooves for receiving the coating substance. Examples of the non-stick material include poly(tetrafluor ethylene), fluorinated ethylene propylene, poly(vinylidene fluoride), poly(para-xylyene), and polyolefin.

In accordance with another embodiment of the invention, a stent mandrel fixture for supporting a stent during application of a coating substance to the stent is provided, comprising: a first member for contacting a first end of the stent, the first member having a domed shaped end; a second member for contacting a second end of the stent, the second member having a domed shaped end; and a third member connecting the first member to the second member and extending through a longitudinal bore of the stent, wherein the stent can be securely pinched between the domed shaped ends of the first and second members.

In accordance with yet another embodiment of the invention, a stent mandrel fixture for supporting a stent during application of a coating substance to the stent is provided, comprising: a first member for contacting a first end of the stent, the first member having a flat end; a second member for contacting a second end of the stent, the second member having a flat end; and a third member connecting the first member to the second member and extending through a longitudinal bore of the stent, wherein the stent can be securely pinched between the flat ends of the first and second members.

In accordance with another embodiment of the invention, a stent mandrel fixture for supporting a stent during application of a coating substance to the stent is provided, comprising: a first member for contacting a first end of the stent, the first member having grooves for receiving the coating substance; a second member for contacting a second end of the stent, the second member having grooves for receiving the coating substance; and a third member connecting the first member to the second member and extending through a longitudinal bore of the stent, wherein the stent can be securely pinched between the ends of the first and second members. In one embodiment, the first or second member is coned shape and the grooves extend longitudinally across the cone. In another embodiment, the grooves extend around the perimeter of the cone.

In accordance with another aspect of the invention, methods of coating a stent using the above-described fixtures are provided.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

The following description is provided to enable any person having ordinary skill in the art to make and use the invention, and is provided in the context of a particular application and its requirements. Various modifications to the embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Figure 1:
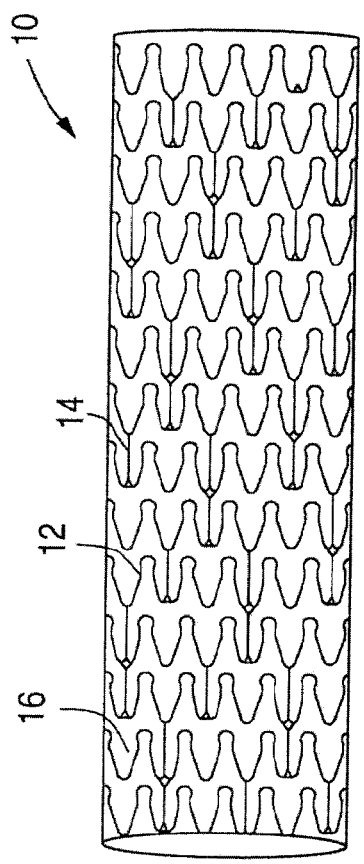
FIG. 1 illustrates a conventional stent.
Figure 2:
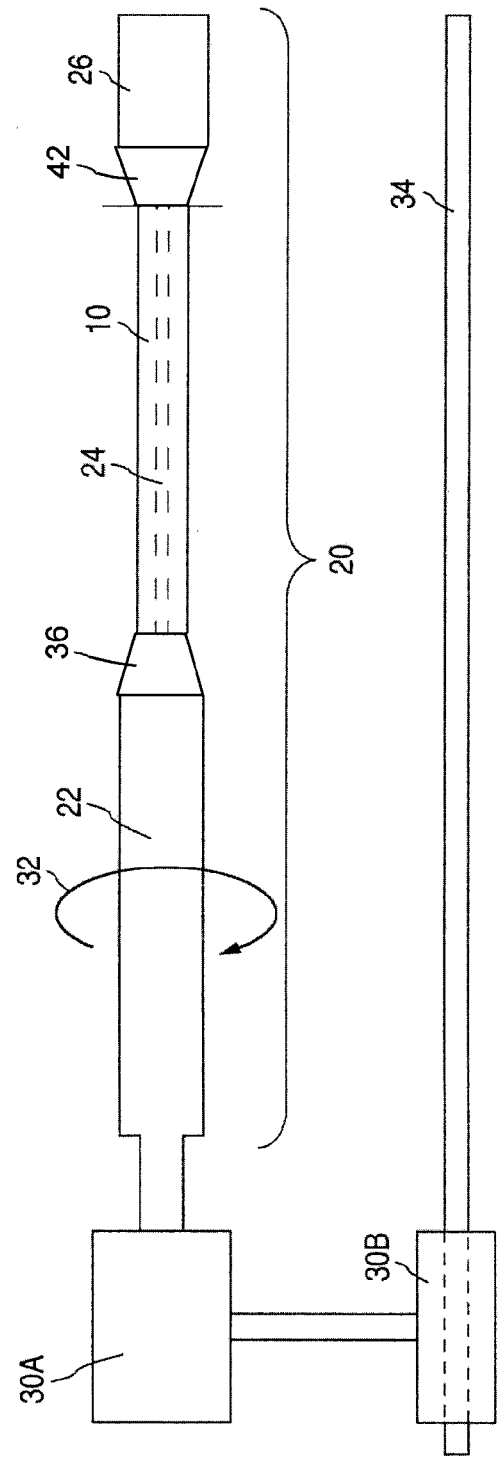
FIG. 2 illustrates a stent mandrel fixture in accordance with an embodiment of the invention.

FIG. 2 illustrates a stent mandrel fixture 20 in accordance with an embodiment of the invention. Fixture 20 for supporting stent 10 is illustrated to include a support member 22, a mandrel 24, and a lock member 26. Support member 22 can connect to a motor 30A so as to provide rotational motion about the longitudinal axis of stent 10, as depicted by arrow 32, during a coating process. Another motor 30B can also be provided for moving support member 22 in a linear direction, back and forth, along a rail 34.

Figure 3:
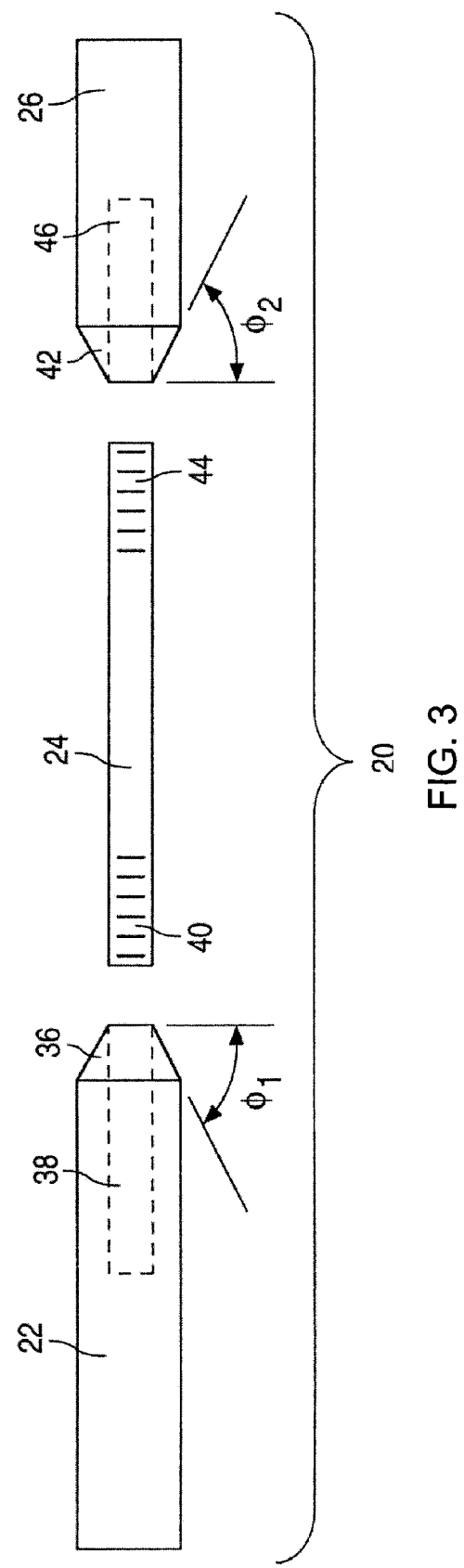
FIG. 3 illustrates an expanded view of stent mandrel fixture of FIG. 2.

FIG. 3 illustrates an expanded view of stent mandrel fixture 20. Support member 22 includes a coning end portion 36, tapering inwardly at an angle $\phi_1$ of about 15° to about 75°, more narrowly from about 30° to about 60°. By way of example, angle $\phi_1$ can be about 45°. In accordance with one embodiment of the invention, mandrel 24 can be permanently affixed to coning end portion 36. Alternatively, support member 22 can include a bore 38 for receiving a first end 40 of mandrel 24. First end 40 of mandrel 24 can be threaded to screw into bore 38 or, alternatively, can be retained within bore 38 by a friction fit. Bore 38 should be deep enough so as to allow mandrel 24 to securely mate with support member 22. The depth of bore 38 can also be over-extended so as to allow a significant length of mandrel 24 to penetrate or screw into bore 38. Bore 38 can also extend completely through support member 22. This would allow the length of mandrel 24 to be adjusted to accommodate stents of various sizes.

The outer diameter of mandrel 24 can be smaller than the inner diameter of stent 10 so as to prevent the outer surface of mandrel 24 from making contact with the inner surface of stent 10. A sufficient clearance between the outer surface of mandrel 24 and the inner surface of stent 10 should be provided to prevent mandrel 24 from obstructing the pattern of the stent body during the coating process. By way of example, the outer diameter of mandrel 24 can be from about 0.010 inches (0.254 mm) to about 0.017 inches (0.432 mm) when stent 10 has an inner diameter of between about 0.025 inches (0.635 mm) and about 0.035 inches (0.889 mm).

Lock member 26 includes a coning end portion 42 having an inwardly tapered angle $\phi_2$. Angle $\phi_2$ can be the same as or different than the above-described angle $\phi_1$. A second end 44 of mandrel 24 can be permanently affixed to lock member 26 if end 40 is disengagable from support member 22. Alternatively, in accordance with another embodiment, mandrel 24 can have a threaded second end 44 for screwing into a bore 46 of lock member 26. Bore 46 can be of any suitable depth that would allow lock member 26 to be incrementally moved closer to support member 22. Bore 46 can also extend completely through lock member 26. Accordingly, stents 10 of any length can be securely pinched between support and lock members 22 and 26. In accordance with yet another embodiment, a non-threaded second end 44 and bore 46 combination is employed such that second end 44 can be press-fitted or friction-fitted within bore 46 to prevent movement of stent 10 on stent mandrel fixture 20.

In order to reduce coating defects, ends 36 and 42 may be coated with one or more polymeric materials having less adhesive force with the coating substance than with members 22 and 26. Examples of a suitable polymeric materials include poly(tetrafluor ethylene) (e.g., Teflon®), fluorinated ethylene propylene ("FEP"), poly(vinylidene fluoride) ("PVDF"), poly(para-xylyene), polyamide (Nylon), polyolefins (e.g., high density poly(ethylene) and poly(propylene)), and polyacetal (Delrin®). In an alternative embodiment of the invention, members 22 and 26 may be made of one or more of the non-stick polymeric materials.

Figure 4:
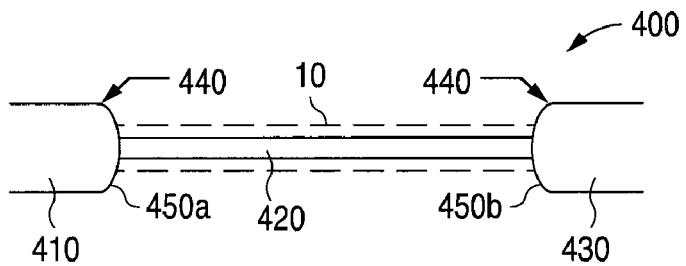
FIG. 4 illustrates a cross section of a second embodiment of a stent mandrel fixture.

FIG. 4 illustrates a cross section of a second embodiment of a stent mandrel fixture 400. Fixture 400 includes a support member 410, a mandrel 420, and a lock member 430. Support member 410 and lock member 430 each have symmetrical ends 440 having surfaces 450a and 450b having a radius of curvature to minimize coating defects by minimizing contact between fixture 400 and stent 10. Curved surfaces 450a and 450b are in essence domed cylindrical protrusions instead of the conical shaped configuration of FIG. 2 and FIG. 3. Curved surface 450a engages one end of stent 10 and curved surface 450b engages the other end of stent 10 so that stent 10 is securely pinched there between. The diameter of curved surfaces 450a and 450b is greater than the outer diameter of stent 10 as positioned between support member 410 and lock member 430.

Figure 5:
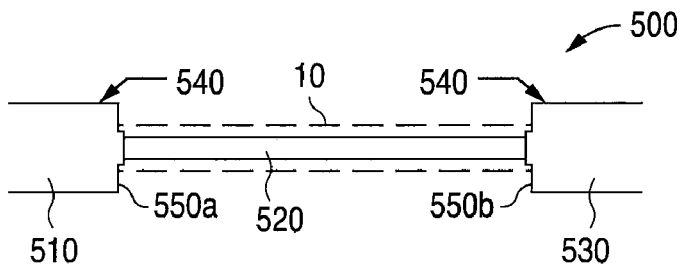
FIG. 5 illustrates a cross section of a third embodiment of a stent mandrel fixture.

FIG. 5 illustrates a cross section of a third embodiment of a stent mandrel fixture 500. Fixture 500 includes a support member 510, a mandrel 520, and a lock member 530. Support member 510 and lock member 530 each have symmetrical ends 540 having surfaces 550a and 550b that have small surface changes. While surfaces 550a and 550b only show a single step, other embodiments of the invention may include surfaces each having a plurality of steps. The unevenness of surfaces 550a and 550b help minimize the formation of coating defects. Surface 550a engages one end of stent 10 and surface 550b engages the other end of stent 10 so that stent 10 is securely pinched there between. The area of surfaces 550a and 550b is greater than the outer diameter of stent 10 positioned between support member 510 and lock member 530.

Figure 6:
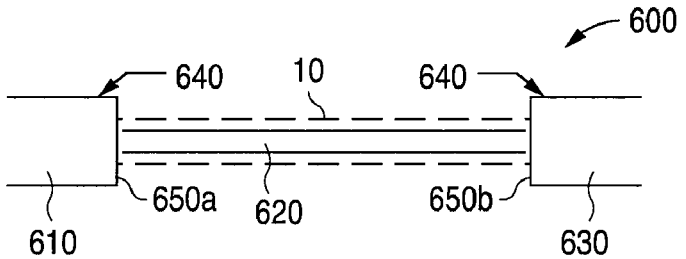
FIG. 6 illustrates a cross section of a fourth embodiment of a stent mandrel fixture.

FIG. 6 illustrates a cross section of a fourth embodiment of a stent mandrel fixture 600. Fixture 600 includes a support member 610, a mandrel 620, and a lock member 630. Support member 610 and lock member 630 each have symmetrical ends 640 having substantially flat surfaces 650a and 650b to minimize coating defects. Surface 650a engages one end of stent 10 and surface 650b engages the other end of stent 10 so that stent 10 is securely pinched there between. The area of surfaces 650a and 650b can be greater than the outer diameter of stent 10 positioned between support member 610 and lock member 630.

Figure 7A:
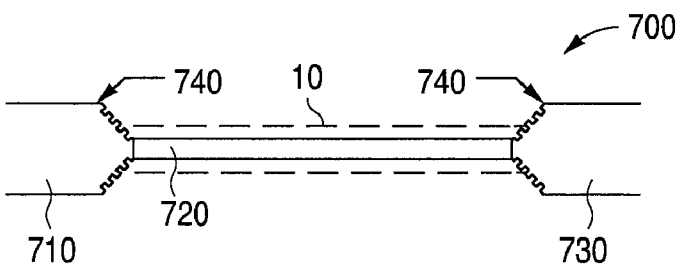
FIG. 7A illustrates a cross section of a fifth embodiment of a stent mandrel fixture.
Figure 7B:
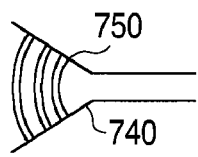
FIG. 7B illustrates a perspective view of the fifth embodiment of the stent mandrel fixture.

FIG. 7A illustrates a cross section of a fifth embodiment of a stent mandrel fixture 700. Fixture 700 includes a support member 710, a mandrel 720, and a lock member 730. Support member 710 and lock member 730 each have symmetrical coned ends 740 having groove designs or channels 750 to minimize coating defects. FIG. 7B illustrates a perspective of a portion of stent mandrel fixture 700. Coned end 740 has grooves or channels 750 circumscribing coned end 740. These grooves or channels 750 enable the flow of composition off coned ends 740 and are deep enough to receive excess composition applied during the coating process.

Figure 8:
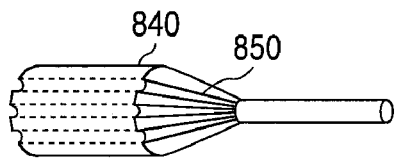
FIG. 8 illustrates a perspective view of a sixth embodiment of a stent mandrel fixture.

FIG. 8 illustrates a perspective view of a sixth embodiment of a stent mandrel fixture. Each end 840 has a grooved design to prevent coating defects from forming at the interface between stent 10 and end 840. Coned ends 840 have grooves or channels extending longitudinally from a distal end of coned end 840 to the proximal end of coned end 840. Any suitable number of channels 850 can be provided around the circumference of coned end 840. Grooves or channels 850 enable the composition to be collected in channels 850. Composition can flow off of coned ends 840, thereby minimizing coating defects.

The foregoing description of the preferred embodiments of the present invention is by way of example only, and other variations and modifications of the above-described embodiments and methods are possible in light of the foregoing teaching. For example, stent mandrel fixtures 400, 500, 600 and 700 may also be coated with a non-stick polymeric material having less adhesive force with the coating substance than with the members.

What is claimed is:

1. A method of coating a stent with a substance, comprising:
    mounting a stent on a stent mandrel fixture, the stent including a first and second end and the stent mandrel fixture including a first member, a second member and a third member, the mounting including placing the first end on a surface of the first member including placing the first end adjacent to or over a groove disposed on the surface of the first member, disposing the third member within a bore of the stent, and placing the second end on the second member; and
    applying the substance to the stent while mounted on the stent mandrel fixture,
    wherein the first member comprises a domed shaped end or a coned end.

2. The method of claim 1, wherein the groove has an opening at the surface and a bottom surface opposite the opening, and wherein the bottom surface of the groove collects an excess amount of the substance.

3. The method of claim 2, wherein the first and second members prevent the stent from sliding off of the third member.

4. The method of claim 1, wherein the mounting of the stent further includes placing at least one of the first and second ends of the stent on a non-stick coating disposed on at least one of the respective first and second members.

5. The method of claim 4, further comprising allowing an excess amount of the applied substance to enter into an opening of the groove and collect at a bottom surface of the groove, the bottom surface located opposite the opening.

6. The method of claim 4, wherein the first and second members prevent the stent from sliding off of the third member.

7. The method of claim 1, wherein the placing of the first end includes placing the first end against the surface of the first member such that the groove extends continuously from a location within the stent bore to a location outside of the stent bore.

8. The method of claim 7, wherein the first member includes a plurality of grooves and the placing of the first end includes placing the first end against a plurality of surfaces, each of the surfaces being disposed between the grooves.

9. The method of claim 8, wherein the plurality of surfaces surround an axis of the bore of the stent.

10. The method of claim 7, further comprising collecting at a bottom surface of the groove an excess amount of the substance applied to the stent.

11. The method of claim 7, wherein the first and second members prevent the stent from sliding off of the third member.

12. The method of claim 1, wherein the groove extends from a position inside the stent to a position outside of the stent.

13. The method of claim 12, further comprising collecting at a bottom surface of the groove an excess amount of the substance applied to the stent.

14. The method of claim 12, wherein the first and second members prevent the stent from sliding off of the third member.

15. The method of claim 1, wherein the first member comprises a coned end such that the groove is disposed on the coned end.

16. The method of claim 1, wherein the first member comprises a domed shaped end.

17. The method of claim 1, wherein the first member comprises a coned end.

18. The method of claim 1, further comprising:
    allowing an excess amount of the substance to flow axially on the first member and off an end of the first member.

19. The method of claim 1, wherein the placing of the first end is performed such that the groove encircles a central axis of the bore.

20. The method of claim 1, wherein a plurality of grooves are disposed on the surface of the first member, wherein each of the plurality of grooves encircles a central axis of the bore.

21. The method of claim 1, wherein at least one of the first or second members is releasably connectable to the third member to allow the stent to be placed over the third member.

22. The method of claim 1, wherein the surface of the first member has a plurality of grooves formed therein, each of the plurality of grooves has an opening at the surface and a bottom surface opposite the opening, and the plurality of grooves collects excess amounts of the substance at the bottom surfaces.

23. The method of claim 22, wherein the placing of the first end is performed such that each of the plurality of grooves extends from a position inside the stent to a position outside the stent.

24. The method of claim 1, wherein the first and second members prevent the stent from sliding off of the third member.

25. A method of coating a stent with a substance, comprising:
    mounting a stent on a stent mandrel fixture, the stent including a first and second end and the stent mandrel fixture including a first member, a second member and a third member, the mounting including placing the first end on the first member including placing the first end on a surface of the first member, the surface having a groove formed therein, the groove having an opening at the surface and a bottom surface opposite the opening, disposing the third member within a bore of the stent, and placing the second end on the second member after the third member is disposed within the bore;

applying the substance to the stent; and collecting an excess amount of the applied substance at the bottom surface of the groove, wherein the mounting of the stent further includes connecting the second member to the third member after the first end is placed on the first member.

26. The method of claim 25, wherein the mounting of the stent further includes displacing the second member relative to the first member after connecting the second member to the third member.

27. The method of claim 25, wherein the mounting of the stent further includes pinching the stent between the first member and the second member including displacing one of the first and second members relative to the other one of the first and second members.

28. The method of claim 27, wherein the pinching of the stent further includes displacing the second member over a threading formed on the third member.

29. The method of claim 27, wherein the pinching of the stent further includes pinching the stent between opposed surfaces of the first and second members, each of the opposed surfaces having grooves formed therein.

30. The method of claim 25, wherein the first and second members prevent the stent from sliding off of the third member.

31. A method of coating a stent with a substance, comprising:

mounting a stent on a stent mandrel fixture, the stent including a first and second end and the stent mandrel fixture including a first member, a second member and a third member, the mounting including placing the first end on the first member including placing the first end adjacent to or over a groove disposed on a surface of the first member, the groove having an opening at the surface and a bottom surface opposite the opening, disposing the third member within a bore of the stent, and placing the second end on the second member; and applying the substance to the stent while mounted on the stent mandrel fixture, wherein the bottom surface of the groove collects an excess amount of the substance, wherein the placing of the first end includes placing the first end against the surface of the first member, and wherein the placing of the first end includes placing the first end against the surface of the first member such that no single, continuous groove extends from a location within the bore of the stent to a location outside of the bore of the stent.

32. The method of claim 31, wherein the first and second members prevent the stent from sliding off of the third member.

33. A method of coating a stent with a substance, comprising:

mounting a stent on a stent mandrel fixture, the stent including a first and second end and the stent mandrel fixture including a first member, a second member and a third member, the mounting including placing the first end on the first member, disposing the third member within a bore of the stent, and placing the second end on the second member; and applying the substance to the stent while mounted on the stent mandrel fixture, wherein the placing of the first end includes placing the first end against the surface of the first member such that the groove circumscribes an axis of the bore of the stent.

34. The method of claim 33, wherein the placing of the first end includes placing the first end against the surface of the first member such that the groove is disposed entirely within the bore of the stent.

35. The method of claim 33, wherein the placing of the first end includes placing the first end against the surface of the first member such that the groove is disposed entirely outside of the bore of the stent.

36. The method of claim 33, further comprising allowing an excess amount of the applied substance to enter into an opening of the groove and collect at a bottom surface of the groove, the bottom surface located opposite the opening.

37. The method of claim 33, wherein the first and second members prevent the stent from sliding off of the third member.

38. A method of coating a stent with a substance, comprising:

mounting a stent on a stent mandrel fixture, the stent including a first and second end and the stent mandrel fixture including a first member, a second member and a third member, the mounting including placing the first end on the first member including placing the first end adjacent to or over a groove disposed on a surface of the first member, the groove having an opening at the surface and a bottom surface opposite the opening, disposing the third member within a bore of the stent, and placing the second end on the second member; and applying the substance to the stent while mounted on the stent mandrel fixture, wherein the bottom surface of the groove collects an excess amount of the substance, wherein the placing of the first end includes placing the first end against the surface of the first member, and wherein the placing of the first end includes placing the first end against the surface of the first member such that a first groove on the surface is disposed entirely outside the bore of the stent and a second groove on the surface is disposed entirely inside the bore of the stent.

39. The method of claim 38, wherein the grooves are channels having walls orientated at right angles to each other.

40. The method of claim 38, wherein the first and second members prevent the stent from sliding off of the third member.

41. A method of coating a stent with a substance, comprising:

mounting a stent on a stent mandrel fixture, the stent including a first and second end and the stent mandrel fixture including a first member, a second member and a third member, the mounting including placing the first end on the first member, disposing the third member within a bore of the stent, and placing the second end on the second member, wherein the placing of the first end includes placing the first end adjacent to or over a groove disposed on the surface of the first member, the groove has an opening at the surface and a bottom surface opposite the opening, and wherein the placing of the first end is performed such that the groove extends from a position inside the stent to a position outside of the stent; and applying the substance to the stent while mounted on the stent mandrel fixture, wherein the groove collects excess amounts of the substance, the groove encircles a central axis of the bore.

42. A method of coating a stent with a substance, comprising:
mounting a stent on a stent mandrel fixture, the stent including a first and second end and the stent mandrel fixture including a first member, a second member and a third member, the mounting including placing the first end on the first member including placing the first end on a surface of the first member, the surface having a groove formed therein, the groove having an opening at the surface and a bottom surface opposite the opening, disposing the third member within a bore of the stent, and placing the second end on the second member after the third member is disposed within the bore;
applying the substance to the stent; and
collecting an excess amount of the applied substance at the bottom surface of the groove,
wherein the surface of the first member has a plurality of grooves formed therein, each of the plurality of grooves has an opening at the surface and a bottom surface opposite the opening, and the plurality of grooves collects excess amounts of the substance at the bottom surfaces, and
each of the plurality of grooves encircles a central axis of the bore.

43. A method of coating a stent with a substance, comprising:
mounting a stent on a stent mandrel fixture, the stent including a first and second end and the stent mandrel fixture including a first member, a second member and a third member, the mounting including placing the first end on the first member including placing the first end adjacent to or over a groove disposed on a surface of the first member, disposing the third member within a bore of the stent, and placing the second end on the second member;
applying the substance to the stent while mounted on the stent mandrel fixture; and
allowing an excess amount of the applied substance to enter into an opening of the groove and collect at a bottom surface of the groove, the bottom surface located opposite the opening; and allowing the excess amount to flow axially on the first member and off an end of the first member,
wherein the mounting of the stent further includes placing at least one of the first and second ends of the stent on a non-stick coating disposed on at least one of the respective first and second members.

44. A method of coating a stent with a substance, comprising:
mounting a stent on a stent mandrel fixture, the stent including a first and second end and the stent mandrel fixture including a first member, a second member and a third member, the mounting including placing the first end on the first member including placing the first end adjacent to or over a groove disposed on a surface of the first member, the groove having an opening at the surface and a bottom surface opposite the opening, disposing the third member within a bore of the stent, and placing the second end on the second member; and
applying the substance to the stent while mounted on the stent mandrel fixture, wherein the bottom surface of the groove collects an excess amount of the substance, wherein at least one of the first or second members is releasably connectable to the third member to allow the stent to be placed over the third member.

45. A method of coating a stent with a substance, comprising:
mounting a stent on a stent mandrel fixture, the stent including a first and second end and the stent mandrel fixture including a first member, a second member and a third member, the mounting including placing the first end on the first member including placing the first end adjacent to or over a groove disposed on a surface of the first member, disposing the third member within a bore of the stent, and placing the second end on the second member; and
applying the substance to the stent while mounted on the stent mandrel fixture,
wherein the mounting of the stent further includes placing at least one of the first and second ends of the stent on a non-stick coating disposed on at least one of the respective first and second members, and wherein at least one of the first or second members is releasably connectable to the third member to allow the stent to be placed over the third member.

46. A method of coating a stent with a substance, comprising:
mounting a stent on a stent mandrel fixture, the stent including a first and second end and the stent mandrel fixture including a first member, a second member and a third member, the mounting including placing the first end on the first member including placing the first end on a surface of the first member, the surface having a groove formed therein, the groove having an opening at the surface and a bottom surface opposite the opening, disposing the third member within a bore of the stent, and placing the second end on the second member after the third member is disposed within the bore;
applying the substance to the stent; and
collecting an excess amount of the applied substance at the bottom surface of the groove,
wherein at least one of the first or second members is releasably connectable to the third member to allow the stent to be placed over the third member.

47. A method of coating a stent with a substance, comprising:
mounting a stent on a stent mandrel fixture, the stent including a first and second end and the stent mandrel fixture including a first member, a second member and a third member, the mounting including placing the first end on the first member including placing the first end adjacent to or over a groove disposed on a surface of the first member, disposing the third member within a bore of the stent, and placing the second end on the second member; and
applying the substance to the stent while mounted on the stent mandrel fixture,
wherein the placing of the first end includes placing the first end against the surface of the first member such that the groove extends continuously from a location within the stent bore to a location outside of the stent bore, and
wherein at least one of the first or second members is releasably connectable to the third member to allow the stent to be placed over the third member.

48. A method of coating a stent with a substance, comprising:
mounting a stent on a stent mandrel fixture, the stent including a first and second end and the stent mandrel fixture including a first member, a second member and a third member, the mounting including placing the first end on the first member, disposing the third member within a bore of the stent, and placing the second end on the second member, wherein the placing of the first end includes placing the first end adjacent to or over a plurality of grooves disposed on the surface of the first member, each of the plurality of grooves has an opening at the surface and a bottom surface opposite the opening, and wherein the placing of the first end is performed such that each of the plurality of grooves extends from a position inside the stent to a position outside of the stent; and applying the substance to the stent while mounted on the stent mandrel fixture, wherein a groove collects excess amounts of the substance, wherein at least one of the first or second members is releasably connectable to the third member to allow the stent to be placed over the third member.

* * * * *